United States Patent
Duhay et al.

(10) Patent No.: US 10,758,353 B2
(45) Date of Patent: *Sep. 1, 2020

(54) DEVICES, SYSTEMS AND METHODS FOR ACCURATE POSITIONING OF A PROSTHETIC VALVE

(71) Applicant: Edwards Lifesciences Corporation, Irvine, CA (US)

(72) Inventors: Francis G. Duhay, Irvine, CA (US); David L. Zollinger, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 146 days.

This patent is subject to a terminal disclaimer.

(21) Appl. No.: 16/010,348

(22) Filed: Jun. 15, 2018

(65) Prior Publication Data

US 2018/0296337 A1    Oct. 18, 2018

Related U.S. Application Data (63) Continuation of application No. 15/197,559, filed on Jun. 29, 2016, now Pat. No. 9,999,503, which is a
(Continued)

(51) Int. Cl.
*A61F 2/24* (2006.01)

(52) U.S. Cl.
CPC .......... *A61F 2/2436* (2013.01); *A61F 2/2418* (2013.01); *A61F 2/2433* (2013.01); *A61F 2/2475* (2013.01); *A61F 2230/0054* (2013.01)

(58) Field of Classification Search
CPC .... A61F 2/2418; A61F 2/2433; A61F 2/2436; A61F 2230/0054
See application file for complete search history.

(56) References Cited

U.S. PATENT DOCUMENTS

| 4,378,224 A | 3/1983 | Nimni et al. |
| 4,553,974 A | 11/1985 | Dewanjee |

(Continued)

FOREIGN PATENT DOCUMENTS

| DE | 19907646 A1 | 8/2000 |
| EP | 0815805 A2 | 1/1998 |

(Continued)

OTHER PUBLICATIONS

Boudjemline et al., Steps Toward Percutaneous Aortic Valve Replacement, Circulation 2002;105: 775-778.
(Continued)

*Primary Examiner* — Ashley L Fishback
(74) *Attorney, Agent, or Firm* — Scott R. Hansen; Joel B. German (57) ABSTRACT

The invention is a system and method for accurately positioning a prosthetic valve such as a prosthetic heart valve at a desired position for deployment. The invention includes extendable positioning elements which provide tactile feedback to a user to confirm proper positioning of the catheter with respect to the native valve annulus. During delivery, the extendable positioning elements may lie against or near the catheter, over the prosthetic valve and expandable balloon, providing a low profile for advancing the catheter to the desired treatment location via small passages such as body lumens. Prior to valve deployment, the positioning elements are extended and brought into contact with tissue of the native annulus to confirm the proper positioning of the delivery system and prosthetic valve.

22 Claims, 8 Drawing Sheets

Related U.S. Application Data continuation of application No. 13/432,901, filed on Mar. 28, 2012, now Pat. No. 9,381,082.

(60) Provisional application No. 61/478,109, filed on Apr. 22, 2011.

(56) References Cited

U.S. PATENT DOCUMENTS

| | | | |
|---|---|---|---|
| 4,573,470 A | 3/1986 | Samson et al. |
| 4,582,181 A | 4/1986 | Samson |
| 4,605,002 A | 8/1986 | Rebuffat |
| 4,647,283 A | 3/1987 | Carpentier et al. |
| 4,648,881 A | 3/1987 | Carpentier et al. |
| 4,753,652 A | 6/1988 | Langer et al. |
| 4,944,740 A | 7/1990 | Buchbinder et al. |
| 5,059,186 A | 10/1991 | Yamamoto et al. |
| 5,125,895 A | 6/1992 | Buchbinder et al. |
| 5,188,636 A | 2/1993 | Fedotov |
| 5,304,184 A | 4/1994 | Hathaway et al. |
| 5,306,234 A | 4/1994 | Johnson |
| 5,318,587 A | 6/1994 | Davey |
| 5,320,632 A | 6/1994 | Heidmueller |
| 5,350,361 A | 9/1994 | Tsukashima et al. |
| 5,364,408 A | 11/1994 | Gordon |
| 5,368,601 A | 11/1994 | Sauer et al. |
| 5,370,685 A | 12/1994 | Stevens |
| 5,374,275 A | 12/1994 | Bradley et al. |
| 5,403,329 A | 4/1995 | Hinchcliffe |
| 5,417,699 A | 5/1995 | Klein et al. |
| 5,417,700 A | 5/1995 | Egan |
| 5,425,737 A | 6/1995 | Burbank et al. |
| 5,431,666 A | 7/1995 | Sauer et al. |
| 5,458,572 A | 10/1995 | Campbell et al. |
| 5,527,322 A | 6/1996 | Klein et al. |
| 5,537,322 A | 7/1996 | Denz et al. |
| 5,545,214 A | 8/1996 | Stevens |
| 5,571,215 A | 11/1996 | Sterman et al. |
| 5,713,951 A | 2/1998 | Garrison et al. |
| 5,718,725 A | 2/1998 | Sterman et al. |
| 5,792,152 A | 8/1998 | Klein et al. |
| 5,792,172 A | 8/1998 | Fischell et al. |
| 5,797,960 A | 8/1998 | Stevens et al. |
| 5,810,850 A | 9/1998 | Hathaway et al. |
| 5,820,631 A | 10/1998 | Nobles |
| 5,860,990 A | 1/1999 | Nobles et al. |
| 5,891,159 A | 4/1999 | Sherman et al. |
| 5,924,424 A | 7/1999 | Stevens et al. |
| 5,968,068 A | 10/1999 | Dehdashtian et al. |
| 5,972,005 A | 10/1999 | Stalker et al. |
| 5,972,030 A | 10/1999 | Garrison et al. |
| 6,001,056 A | 12/1999 | Jassawalla et al. |
| 6,013,092 A | 1/2000 | Dehdashtian et al. |
| 6,033,378 A | 3/2000 | Lundquist et al. |
| 6,071,273 A | 6/2000 | Euteneuer et al. |
| 6,083,257 A | 7/2000 | Taylor et al. |
| 6,106,540 A | 8/2000 | White et al. |
| 6,117,144 A | 9/2000 | Nobles et al. |
| 6,143,004 A | 11/2000 | Davis et al. |
| 6,146,325 A | 11/2000 | Lewis et al. |
| 6,206,893 B1 | 3/2001 | Klein et al. |
| 6,231,563 B1 | 5/2001 | White et al. |
| 6,245,079 B1 | 6/2001 | Nobles et al. |
| 6,251,092 B1 | 6/2001 | Qin et al. |
| 6,269,819 B1 | 8/2001 | Oz et al. |
| 6,358,258 B1 | 3/2002 | Arcia et al. |
| 6,379,372 B1 | 4/2002 | Dehdashtian et al. |
| 6,425,916 B1 | 7/2002 | Garrison et al. |
| 6,454,777 B1 | 9/2002 | Green |
| 6,506,339 B1 | 1/2003 | Girardot et al. |
| 6,517,553 B2 | 2/2003 | Klein et al. |
| 6,540,782 B1 | 4/2003 | Snyders |
| 6,551,331 B2 | 4/2003 | Nobles et al. |
| 6,558,418 B2 | 5/2003 | Carpentier et al. |
| 6,562,052 B2 | 5/2003 | Nobles et al. |
| 6,591,472 B1 | 7/2003 | Noone et al. |
| 6,679,268 B2 | 1/2004 | Stevens et al. |
| 6,682,558 B2 | 1/2004 | Tu et al. |
| 6,702,255 B2 | 3/2004 | Dehdashtian |
| 6,716,207 B2 | 4/2004 | Farnholtz |
| 6,726,717 B2 | 4/2004 | Alfieri et al. |
| 6,730,118 B2 | 5/2004 | Spenser et al. |
| 6,733,509 B2 | 5/2004 | Nobles et al. |
| 6,743,239 B1 | 6/2004 | Kuehn et al. |
| 6,746,471 B2 | 6/2004 | Mortier et al. |
| 6,749,630 B2 | 6/2004 | McCarthy et al. |
| 6,805,710 B2 | 10/2004 | Bolling et al. |
| 6,821,297 B2 | 11/2004 | Snyders |
| 6,830,584 B1 | 12/2004 | Seguin |
| 6,858,039 B2 | 2/2005 | McCarthy |
| 6,890,330 B2 | 5/2005 | Streeter et al. |
| 6,893,460 B2 | 5/2005 | Spenser et al. |
| 6,899,704 B2 | 5/2005 | Sterman et al. |
| 6,908,481 B2 | 6/2005 | Cribier |
| 6,911,034 B2 | 6/2005 | Nobles et al. |
| 6,978,176 B2 | 12/2005 | Lattouf |
| 6,994,666 B2 | 2/2006 | Shannon et al. |
| 7,004,952 B2 | 2/2006 | Nobles et al. |
| 7,078,163 B2 | 7/2006 | Torrianni |
| 7,090,686 B2 | 8/2006 | Nobles et al. |
| 7,100,614 B2 | 9/2006 | Stevens et al. |
| 7,160,322 B2 | 1/2007 | Gabbay |
| 7,201,772 B2 | 4/2007 | Schwammenthal et al. |
| 7,273,468 B2 | 9/2007 | Bedell |
| 7,276,078 B2 | 10/2007 | Spenser et al. |
| 7,294,148 B2 | 11/2007 | McCarthy |
| 7,323,004 B2 | 1/2008 | Parihar |
| 7,373,207 B2 | 5/2008 | Lattouf |
| 7,377,926 B2 | 5/2008 | Topper et al. |
| 7,399,315 B2 | 7/2008 | Iobbi |
| 7,510,572 B2 | 3/2009 | Gabbay |
| 7,513,908 B2 | 4/2009 | Lattouf |
| 7,534,260 B2 | 5/2009 | Lattouf |
| 7,569,062 B1 | 8/2009 | Kuehn et al. |
| 7,604,650 B2 | 10/2009 | Bergheim |
| 7,611,535 B2 | 11/2009 | Woolfson et al. |
| 7,648,528 B2 | 1/2010 | Styrc |
| 7,780,723 B2 | 8/2010 | Taylor |
| 7,803,167 B2 | 9/2010 | Nobles et al. |
| 7,803,185 B2 | 9/2010 | Gabbay |
| 7,905,892 B2 | 3/2011 | Nobles et al. |
| 8,075,606 B2 | 12/2011 | Dorn |
| 8,182,530 B2 | 5/2012 | Huber |
| 9,381,082 B2 | 7/2016 | Duhay et al. |
| 2001/0001812 A1 | 5/2001 | Valley et al. |
| 2001/0025643 A1 | 10/2001 | Foley |
| 2002/0026233 A1 | 2/2002 | Shaknovich |
| 2002/0032481 A1 | 3/2002 | Gabbay |
| 2002/0123802 A1 | 9/2002 | Snyders |
| 2002/0128707 A1 | 9/2002 | Kavteladze et al. |
| 2002/0165571 A1 | 11/2002 | Hebert et al. |
| 2002/0183839 A1 | 12/2002 | Garrison et al. |
| 2003/0040792 A1 | 2/2003 | Gabbay |
| 2003/0109924 A1 | 6/2003 | Cribier |
| 2003/0114913 A1 | 6/2003 | Spenser et al. |
| 2003/0130571 A1 | 7/2003 | Lattouf |
| 2003/0163194 A1 | 8/2003 | Quijano et al. |
| 2003/0199975 A1 | 10/2003 | Gabbay |
| 2004/0034411 A1 | 2/2004 | Quijano et al. |
| 2004/0039436 A1 | 2/2004 | Spenser et al. |
| 2004/0162608 A1 | 8/2004 | Haverich |
| 2004/0215139 A1 | 10/2004 | Cohen |
| 2004/0260309 A1 | 12/2004 | Packard |
| 2005/0043791 A1 | 2/2005 | McCarthy et al. |
| 2005/0049698 A1 | 3/2005 | Bolling et al. |
| 2005/0070844 A1 | 3/2005 | Chow et al. |
| 2005/0075729 A1 | 4/2005 | Nguyen et al. |
| 2005/0131533 A1 | 6/2005 | Alfieri et al. |
| 2005/0137695 A1 | 6/2005 | Salahieh et al. |
| 2005/0148997 A1 | 7/2005 | Valley et al. |
| 2005/0209671 A1 | 9/2005 | Ton et al. |
| 2005/0228407 A1 | 10/2005 | Nobles et al. |
| 2005/0240200 A1 | 10/2005 | Bergheim |
| 2005/0251251 A1 | 11/2005 | Cribier |
| 2005/0271544 A1 | 12/2005 | Benesch et al. |

(56) References Cited

U.S. PATENT DOCUMENTS

| | | |
|---|---|---|
| 2005/0271844 A1 | 12/2005 | Mapes et al. |
| 2006/0004439 A1 | 1/2006 | Spenser et al. |
| 2006/0036313 A1 | 2/2006 | Vassiliades |
| 2006/0074484 A1 | 4/2006 | Huber |
| 2006/0142848 A1 | 6/2006 | Gabbay |
| 2006/0149360 A1 | 7/2006 | Schwammenthal et al. |
| 2006/0178675 A1 | 8/2006 | Hamman |
| 2006/0195120 A1 | 8/2006 | Nobles et al. |
| 2006/0212056 A1 | 9/2006 | Salvadori et al. |
| 2006/0217803 A1 | 9/2006 | Ingle et al. |
| 2006/0271064 A1 | 11/2006 | Agnew |
| 2006/0276889 A1 | 12/2006 | Chambers et al. |
| 2006/0282102 A1 | 12/2006 | Nobles et al. |
| 2006/0293745 A1 | 12/2006 | Carpentier et al. |
| 2007/0005131 A1 | 1/2007 | Taylor |
| 2007/0010829 A1 | 1/2007 | Nobles et al. |
| 2007/0021828 A1 | 1/2007 | Krolik et al. |
| 2007/0043385 A1 | 2/2007 | Nobles et al. |
| 2007/0112422 A1 | 5/2007 | Dehdashtian |
| 2007/0123979 A1 | 5/2007 | Perier et al. |
| 2007/0149987 A1 | 6/2007 | Wellman et al. |
| 2007/0203479 A1 | 8/2007 | Auth et al. |
| 2007/0203506 A1 | 8/2007 | Sibbitt et al. |
| 2007/0208550 A1 | 9/2007 | Cao et al. |
| 2007/0276413 A1 | 11/2007 | Nobles |
| 2007/0276414 A1 | 11/2007 | Nobles |
| 2008/0004597 A1 | 1/2008 | Lattouf et al. |
| 2008/0033459 A1 | 2/2008 | Shafi et al. |
| 2008/0058839 A1 | 3/2008 | Nobles et al. |
| 2008/0071362 A1 | 3/2008 | Tuval et al. |
| 2008/0188873 A1 | 8/2008 | Speziali |
| 2008/0269786 A1 | 10/2008 | Nobles et al. |
| 2009/0099578 A1 | 4/2009 | Heneveld et al. |
| 2009/0240264 A1 | 9/2009 | Tuval et al. |
| 2009/0287182 A1 | 11/2009 | Bishop et al. |
| 2009/0287183 A1 | 11/2009 | Bishop et al. |
| 2010/0030242 A1 | 2/2010 | Nobles et al. |
| 2010/0249916 A1 | 9/2010 | Zhang |

FOREIGN PATENT DOCUMENTS

| | | |
|---|---|---|
| EP | 0941698 A1 | 9/1999 |
| EP | 1356793 A2 | 10/2003 |
| EP | 1447111 A1 | 8/2004 |
| EP | 1570790 A2 | 9/2005 |
| EP | 2114318 A1 | 11/2009 |
| EP | 2120794 A1 | 11/2009 |
| FR | 2945440 A1 | 11/2010 |
| GB | 2335146 A | 9/1999 |
| WO | 9413211 A1 | 6/1994 |
| WO | 9503742 A1 | 2/1995 |
| WO | 9513021 A1 | 5/1995 |
| WO | 9640347 A1 | 12/1996 |
| WO | 9903904 A1 | 1/1999 |
| WO | 0108050 A1 | 2/2001 |
| WO | 0126724 A2 | 4/2001 |
| WO | 2004019825 A1 | 3/2004 |
| WO | 2005034801 A2 | 4/2005 |
| WO | 2005102015 A2 | 11/2005 |
| WO | 2005107650 A2 | 11/2005 |
| WO | 2006019798 A1 | 2/2006 |
| WO | 2006023676 A1 | 3/2006 |
| WO | 2006041505 A1 | 4/2006 |
| WO | 2006127765 A1 | 11/2006 |
| WO | 2006138173 A2 | 12/2006 |
| WO | 2007002920 A2 | 1/2007 |
| WO | 2008058519 A1 | 5/2008 |

OTHER PUBLICATIONS

Brodsky, Percutaneous Approaches to Aortic Valve Replacement, Cardiac Interventions, Dec. 2004, pp. 4-9.

Cooley, Presidential Address: How Long Will the Heart Still Beat?, Cardiovascular Surgical Society, Texas Heart Institute, vol. 32, No. 2, 2005, pp. 126-129.

Cribier et al., "Percutaneous Transcatheter Implantation of an Aortic Valve Prosthesis for Calcific Aortic Stenosis: First Human Case Description," Circulation, vol. 106, pp. 3006-3008 (2002).

Dewey, et al., Feasibility of a Trans-Apical Approach for Aortic Valve Implantation Using a Device Delivered Valve, Abstract Presentation at ISMICS 8.sup.th Annual Meeting, Jun. 1-4, 2005 New York (pp. 1-2—of flier also attached).

Ferrari, M., et al., Transarterial Aortic Valve Replacement With a Self-Expanding Stent in Pigs. Heart 2004 90: 1326-1331.

Greer, et al., Skeletal Muscle Ventricles, Left Ventricular Apex-to-Aorta Configuration: 1-11 Weeks in Circulation, Circulation 95(2): 497-502.

Gundry, "Aortic Valve Replacement by Mini-Sternotomy," Operative Techniques in Cardiac & Thoracic Surgery, vol. 3, No. 1 (February), pp. 47-53 (1998).

Huber et al., "Do valved stents compromise coronary flow?" Eur. J. Cardiothorac. Surg., vol. 25, pp. 754-759 (2004).

Huber et al., "Ultrasound Navigation Through the Heart for Off-Pump Aortic Valved Stent Implantation: New Tools for New Goals," J. Endovase. Ther., vol. 11, pp. 503-510 (2004).

Huber, et al., Direct-Access Valve Replacement a Novel Approach for Off-Pump Valve Implantation Using Valved Stents, JACC, vol. 46, No. 2, 2005, pp. 366-370, www.content.onlinejacc.org by Susan Porter on Sep. 27, 2005.

Huber and Feldman, Transcatheter Valve Therapies, Chapter 6, "Access to the Aortic Valves," pp. 80-100 (2010).

Jamieson et al, "Antegrade placement of the aortic valve stent: transventricular delivery with the Entrata.TM. system," EuroIntervention, supplements 1 (supplement A) pp. A14-A18 (2006).

Leipzig Flyer, Pioneering Techniques in Cardiac Surgery, Heart Center Leipzig Auditorium, Leipzig, Germany, Dec. 1-2, 2005.

Lutter et al., Percutaneous Valve Replacement: Current State and Future Prospects, Ann Throac Surg 2004; 78:2199-2206.

Ma, et al., Double-crowned valved stents for off-pump mital valve repalcement, European Journal of Cardio-Thoracic Surgery 28 (2005) pp. 194-199.

Morgan et al., "Left Heart Catheterization by Direct Ventricular Puncture: Withstanding the Test of Time," Catheterization and Cardiovascular Diagnosis, vol. 16, pp. 87-90 (1989).

Sarnoff et al., "The Surgical Relief of Aortic Stenosis by Means of Apical—Aortic Valvular Anastomosis," Circulation, vol. 11, pp. 564-575 (1955).

Semple et al., "Left Heart Catheterization by Direct Ventricular Puncture," Brit. Heart J., vol. 30, pp. 402-406 (1968).

Shanebrook et al., Hemodynamics of Left Ventricular Apex-Aortic Valved Conduits, Cardiovascular Diseases, vol. 6, No. 4, Dec. 1979, 425-438.

Turgut et al., "Left Ventricular Apical Puncture: A Procedure Surviving Well Into the New Millennium," Catheterization and Cardiovascular Interventions, vol. 49, pp. 68-73 (2000).

Vahanian and Palacios, "Percutaneous Approaches to Valvular Disease," Circulation, vol. 109, pp. 1572-1579 (2004).

Vassiliades, "Off-pump apicoaortic conduit insertion for high-risk patients with aortic stenosis," Eur. J. Cardiothorac. Surg., vol. 23, pp. 156-158 (2003).

Walsh, "Interventional cardiology," Current Paediatrics, vol. 14, pp. 45-50 (2004).

Walther, et al., Minimally Invasive Transapical Beating Heart Aortic Valve Implantation—Proof of Concept, European Journal of Cardio-Thoracic Surgery, 2007;31:9-15.

Webb et al., "Percutaneous Stent-Mounted Valve for Treatment of Aortic or Pulmonary Valve Disease," Catheterization and Cardiovascular Interventions, vol. 63, pp. 89-93 (2004).

Wellens, How Long Will the Heart Still Beat?, Texas Heart Institute Journal, vol. 32, No. 2, 2005, pp. 126-129.

Zhou et al., Self-expandable Valved Stent of Large Size: Off-bypass implantation in Pulmonary Position, European Journal of Cardiothoracic Surgery 24 (2003) 212-216.

Fig. 13B ized, and endoscopic minimally invasive surgery. The valve prosthesis can be also applied to other body channels provided with native valves, such as veins or in organs (liver, intestine, urethra, etc.).

DEVICES, SYSTEMS AND METHODS FOR ACCURATE POSITIONING OF A PROSTHETIC VALVE

CROSS-REFERENCE TO RELATED APPLICATIONS

The present application is a continuation of U.S. patent application Ser. No. 15/197,559, filed Jun. 29, 2016, now U.S. Pat. No. 9,999,503, which is a continuation of U.S. patent application Ser. No. 13/432,901, filed Mar. 28, 2012, now U.S. Pat. No. 9,381,082, which claims priority under 35 U.S.C. 119(e) to U.S. Provisional Application Ser. No. 61/478,109, filed Apr. 22, 2011, all of which are incorporated by reference herein.

FIELD OF THE INVENTION

The present invention relates to methods and devices for delivering a valve prosthesis for implantation in body channels, including, but not limited to, a cardiac valve prosthesis to be implanted by surgical procedures such as open surgery, percutaneous procedures such as transcutaneous catheterization, and endoscopic minimally invasive surgery. The valve prosthesis can be also applied to other body channels provided with native valves, such as veins or in organs (liver, intestine, urethra, etc.).

BACKGROUND

The present invention relates to systems used to deliver a prosthetic valve to a heart. More specifically, the present invention is directed to an improved delivery system for delivery of a prosthetic valve to a human heart.

Catheters for prosthetic heart valve implantation are known in the art and have been commonly used to reach locations inside the body that are not readily accessible by surgery or where access without surgery is desirable. Numerous transcatheter techniques are known in the art, including techniques which are percutaneous, trans-arterial, trans-venous, trans-cardiac, trans-atrial, trans-ventricular, and/or trans-apical. A key factor in such transcatheter heart valve deployment is properly positioning the prosthetic implant, e.g., accurately positioning a prosthetic heart valve within the native heart valve annulus.

Over the years, a variety of techniques have been proposed and/or used for facilitating proper positioning of catheters. For example, current transcatheter valve implantation systems, such as the Edwards SAPIEN™ Transcatheter Heart Valve, use fluoroscopy and/or echography to properly position the valve within the native valve annulus prior to deployment. Such imaging modalities involve extensive and complicated equipment, and may also have limitations in their accuracy in some circumstances. Improvements may be desired which, when compared to known techniques, may provide improved accuracy, reduced cost/complexity, and/or backup positioning (when used in combination with known techniques).

Prior art methods also include modifications to the implant itself. For example, some transcatheter valve implantation systems employ retractable metal positioners that extend from the valve frame. For example, U.S. Pat. Nos. 7,201,772 and 7,399,315, as well as US Patent Publication No. 2008/0071362, disclose the use of positioners which are an integral component of the prosthetic heart valve frame. The positioners add extra material to the prosthetic heart valve. Also, upon deployment of the prosthetic heart valve in the patient, the positioners remained in the patient.

Another approach includes the filling (via injection, etc.) of a portion of the prosthetic implant itself with a radiographic contrast solution. After the surgeon or other user has properly positioned and deployed the implant, the radiographic contrast solution is pumped out and replaced with a hardening agent which increases the stiffness of the implant in order to aid in retaining the implant at the desired position. Such a technique is relatively complex.

Although a variety of prosthetic valve positioning methods and systems have been proposed over the years, each of the existing methods and systems has shortcomings. Additionally, improved methods and systems may be used in combination with previously-known methods in order to achieve improved accuracy and/or reliability. Accordingly, an urgent need exists for an improved valve positioning method and system which is versatile, reliable, and easy to use. The present invention addresses this need.

BRIEF SUMMARY OF THE INVENTION

Preferred embodiments of the present invention provide a heart valve delivery system for delivery of a prosthetic (i.e., replacement) heart valve to a native valve site within the human vasculature. The delivery system includes a delivery catheter having one or more extendable positioning limbs configured to be selectively and radially extended from the catheter body.

In an exemplary embodiment of the invention, positioning elements are incorporated into the valve delivery catheter itself. The positioning elements may be configured to be radially expanded and/or longitudinally displaced with respect to other elements of the valve delivery catheter.

In one exemplary embodiment of the invention, a prosthetic heart valve is positioned on a distal portion of a delivery catheter. One or more extendable limbs are also positioned on the delivery catheter. Each extendable limb extends from a fixed end to a free end, with the fixed end secured to the delivery catheter. The fixed end is secured to the delivery catheter at a position which is longitudinally displaced from the prosthetic heart valve, with the free end positioned longitudinally adjacent the prosthetic heart valve, such that the extendable limb extends over at least a portion of the length of the prosthetic heart valve. The extendable limb is configured to transform from a restrained position wherein the free end is positioned tightly against the catheter body to an extended position wherein the free end is radially extended away from the catheter body.

The extendable limbs may be spring-loaded or otherwise configured such that, when the limb is radially unrestrained, the free ends thereof will revert to a position wherein the free ends are radially extended away from the catheter body. For example, the extendable limbs may be formed from a memory material.

A sliding cuff may be used to restrain the extendable limbs. The sliding cuff may be configured to slide over the extendable limbs starting from a position adjacent the fixed ends of the extendable limbs, with the sliding cuff configured to be slid over the extendable limbs in a direction toward the free ends thereof. The sliding cuff may have an internal diameter sized to permit the sliding cuff to be slid over the catheter and extendable limbs in a relatively tight fashion, such that as the sliding cuff is slid over the extendable limbs the limbs are forced to assume their restrained position wherein the free ends thereof are positioned radially against the catheter.

In one example of a method according to the invention, a prosthetic heart valve is configured for deployment using a balloon. For example, the prosthetic heart valve may comprise a balloon expandable stent supporting a bioprosthetic valve. A delivery catheter may include an expandable balloon at a distal portion of the catheter. Prior to implantation, the prosthetic heart valve is carefully crimped onto the balloon of the delivery catheter of the invention. The positioners, in the form of retractable members, are positioned at least partially over and tightly against the prosthetic valve, such that the overall profile of the catheter distal portion (with expandable balloon, prosthetic valve, and positioners) is relatively low in order to promote easy advancement of the catheter through the body lumen(s). The catheter distal portion (with prosthetic valve thereon) can then be advanced to the desired position for valve deployment. For example, for replacing an aortic valve, the catheter distal portion may be advanced into the patient via the femoral artery and delivered to a native stenotic aortic valve using a retrograde approach, or may be advanced into the patient via an intercostal or other chest opening and into the left ventricular apex to the native stenotic aortic valve using an antegrade approach.

Once the catheter distal portion with prosthetic valve thereon is positioned at the native valve annulus, the positioners are used to refine the positioning. In one embodiment of the invention, the catheter distal portion is advanced distally until the prosthetic heart valve passes through the native valve annulus. The retractable members are then radially deployed away from the catheter. The catheter distal portion is then retracted proximally at least partially back through the native valve annulus until the retractable members engage against the native valve leaflets, valve annulus, and/or other structures. The user then knows that the prosthetic heart valve is at the desired position. The user can then deploy the prosthetic heart valve at the desired position within the native valve annulus. In one embodiment of the invention, the retractable members are pressed between the prosthetic heart valve and native valve annulus when the prosthetic heart valve is deployed. In such an embodiment, after the prosthetic heart valve is properly deployed the catheter distal portion can be advanced once again distally a distance sufficient for the retractable members to slip free of the deployed prosthetic heart valve and native valve annulus. The retractable members are then radially retracted against the catheter distal portion (i.e., to their retracted/delivery state), and the entire catheter assembly can be withdrawn from the heart valve, heart, and patient, leaving the prosthetic valve in proper placement in the heart.

In one embodiment of the invention, after the accurate positioning the catheter within the valve annulus using the retractable member, but prior to actual deployment of the prosthetic heart valve, the retractable members are advanced distally away from the prosthetic heart valve. This advancement of the retractable members occurs while the rest of the catheter remains stationary, i.e., with the prosthetic heart valve held in the desired position for deployment as described above. To distally advance the retractable members while holding the catheter stationary requires the retractable members to be configured for distal displacement with respect to the rest of the catheter, including the portion to which the prosthetic heart valve is secured. For example, the retractable members may be secured to a sliding assembly which permits the retractable members to be distally advanced with respect to the expandable balloon and/or other structures to which the prosthetic heart valve is held on the catheter. In such an embodiment, after the retractable members are advanced distally (but with the prosthetic heart valve still at the selected and accurate deployment position), valve is properly deployed (e.g., by expanding a valve deployment balloon). The retractable members can be radially retracted just before, during, or just after deployment of the prosthetic valve. After the valve is deployed, and with the retractable members radially retracted to their retracted position, the entire catheter assembly can be withdrawn from the heart valve, heart, and patient, leaving the prosthetic valve in proper placement in the heart.

According to one example of a method according to the present invention, a catheter is advanced to a native valve annulus position within the heart of the patient. One or more extendable positioners are positioned at the distal end of the catheter, and move from a first position to a second position that is radially away from the catheter. Tactile or other feedback is used to verify that the prosthetic valve is in proper position in alignment with or adjacent to the native valve annulus. A fixed end of the extendable member is secured to a slidingly-moveable portion that is moveable without requiring movement of the rest of the catheter. After confirming that the prosthetic valve is in proper position and while holding the valve stationary in position, the slidingly-movable portion is slid away until the expandable member is clear of the implant holding section and/or balloon. The prosthetic valve is then deployed into the desired position within the native valve annulus.

The system is well suited for advancing a prosthetic valve into the heart via one or more blood vessels such as the aorta and/or femoral artery, preferably with the retractable members retracted during advancement through the aorta and/or femoral artery and/or other body lumen, but with the retractable members then extended when the system has advanced the prosthetic heart valve to a position at or adjacent the native valve annulus. The system is also well suited for advancing a prosthetic valve into the heart via a surgically-created opening in the heart wall such as an apical puncture, preferably with the retractable members retracted during advancement through the apical puncture, but with the retractable members then extended when the system has advanced the prosthetic heart valve to a position at or adjacent the native valve annulus.

The catheter with prosthetic heart valve and retractable members may be advanced into the heart from a position upstream or downstream of the native heart valve being replaced. The retractable members may be advanced in an expanded configuration toward the native heart valve annulus from a position upstream or downstream of the native heart valve.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

DETAILED DESCRIPTION

Figure 1:
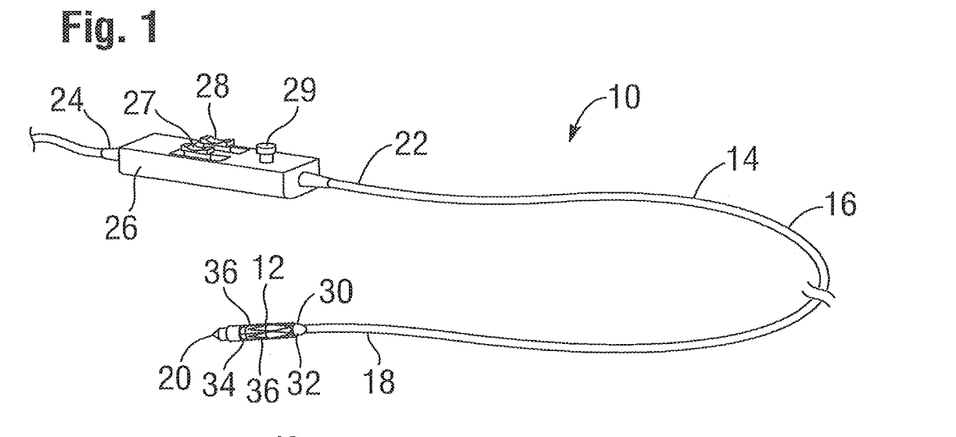
FIG. 1 is a perspective view of a system for replacing a deficient valve according to an embodiment of the invention.

FIG. 1 depicts a delivery system 10 configured to deliver a prosthetic implant such as a prosthetic valve 12 to a selected position using a delivery catheter 14. The delivery catheter 14 comprises a generally elongated catheter main body 16. A catheter distal portion 18 terminates at a catheter distal end 20, and a catheter proximal portion 22 terminates in a catheter proximal end 24. The catheter proximal portion 22 includes a catheter handle 26 which may have one or more controls 27, 28, 29.

The catheter main body 16 may have a usable length (i.e., from the distal end of the handle 26 to the catheter distal end 20) sufficient to permit a user to advance the catheter distal portion 18 with prosthetic valve 12 thereon to a desired position within the patient while the catheter handle 26 remains accessible to the user at a position outside of the patient. For a catheter for delivering a heart valve via a transfemoral approach (via the femoral artery and aorta), the catheter 14 may have a usable length sufficient to reach from an incision in the patient's leg, through the femoral artery, through the aorta, and into the aorta. For such a procedure the catheter usable length may be about 130 cm. With a catheter for delivering a heart valve via an apical approach (e.g., via an intercostal incision in the chest wall and then thru a puncture in the heart apex), the catheter may have a usable length of about 24 inches or less.

The catheter distal portion 18 includes an implant holding section 30 to which the prosthetic valve 12 is positioned. In the particular embodiment depicted, the implant holding section is a catheter balloon 32 configured to be selectively expanded to an enlarged diameter to thereby expand the prosthetic valve 12 to its enlarged/deployed diameter, whereby the prosthetic valve 12 is expanded into contact with the native valve annulus.

Note that the catheter distal portion may include a sheath configured to be slid over the prosthetic valve in its unexpanded/delivery diameter. For a self-expanding prosthetic valve (e.g., a prosthetic valve having a support stent biased to self-expand to an expanded/deployed diameter when released from a restrained/unexpanded configuration, such as a support stent formed from a memory material such as Nitinol), the sheath restrains the prosthetic valve in its unexpanded/delivery diameter. The sheath is further configured to be slid off of the prosthetic valve to release the prosthetic valve. For a self-expanding prosthetic valve, sliding the sheath off of the valve permits the support stent to self-expand to its enlarged/deployment diameter. The sheath may be in addition to or in lieu of an expandable balloon such as that depicted in FIG. 1.

The catheter 14 further comprises a positioner 34 positioned at the catheter distal portion 18. The positioner 34 comprises one or more members 36 which can be radially extended from and/or retracted against the catheter distal end 18.

A user may control operation of the balloon 32, positioner 34, and/or sheath by movement or other activation of one or more of the controls 27, 28, 29 on the handle 26. For example, a first control 27 may control, via sliding movement thereof, extension and/or retraction of the retractable member 36 of the positioned 34. A second control 28 may control, via sliding movement, the sliding advancement/retraction of the sheath. A third control 29 may control the flow of fluid into and/or out of the balloon 32 to inflate and/or deflate the balloon 32.

Figures 2A, 2B:
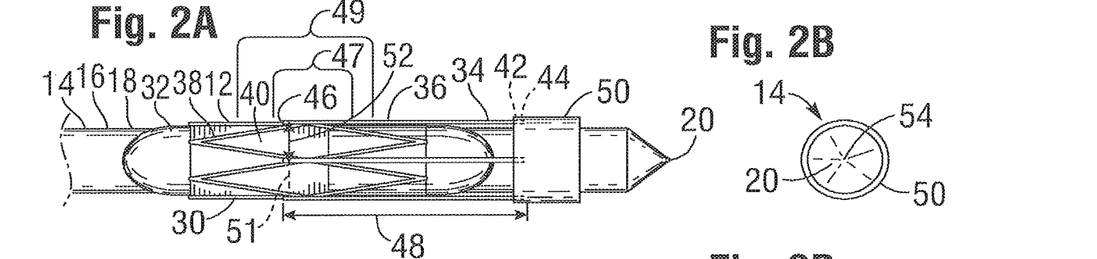
FIGS. 2A-2B depict side and distal end views, respectively, of a distal portion of the system of FIG. 1, with the system in the delivery configuration, according to an embodiment of the invention.

FIGS. 2A-2B depict close-up views of the catheter 14 of FIG. 1, and particularly of the catheter distal portion 18. The prosthetic valve 12 comprises a support stent 38 surrounding prosthetic valve leaflets 40. The prosthetic valve 12 is tightly crimped onto the expandable balloon 32.

The retractable members 36 each have a fixed end 42 secured to the catheter distal portion 18 at a fixed end attachment point 44 which is distal of the implant holding section 30 and of the prosthetic valve 12. The retractable members 36 each have a free end 46, which may be rounded at the tip to prevent unnecessary trauma to tissue when the free end 46 is pressed against same. In the particular embodiment depicted, the retractable members 36 are in their retracted/unexpanded configuration, and extend proximally from the fixed end attachment point 44 to the free end 46. The free end 46 is positioned radially adjacent the catheter distal portion 18 at a position overlying the prosthetic valve 12 and implant holding section 30/expandable balloon 32. In the particular embodiment depicted, when in the retracted position the free end 46 is positioned longitudinally adjacent the middle third portion 47 of the prosthetic valve 12 and also of the middle third portion 49 of the expandable balloon 32 (which in the particular embodiment depict coincides with a middle third portion of the implant holding section 30), with the body of the retractable member 36 passing over a valve annulus alignment position 51 along the length of the prosthetic heart valve 12 which is intended to be aligned with structure of the valve annulus (or other target tissue) against which the member free ends will engage when positioning the device. In a preferred embodiment of the invention, the retractable member 36 has a member length 48 from fixed end attachment point 44 to free end 46 of about 10 to 15 mm.

In the particular embodiment of FIGS. 2A-2B, the catheter 14 includes a cuff 50 configured to be slidingly advanced over and with respect to the retractable members 36. In the embodiment of FIGS. 2A-2B, the cuff 50 is positioned over the retractable members 36, thus holding the retractable members 36 in their retracted/unexpanded position such that the retractable members 36 are held against and generally parallel to the catheter distal portion 18, with the free ends 46 positioned radially adjacent the prosthetic valve 12 and balloon 32.

Figures 3A, 3B, 4A, 4B:
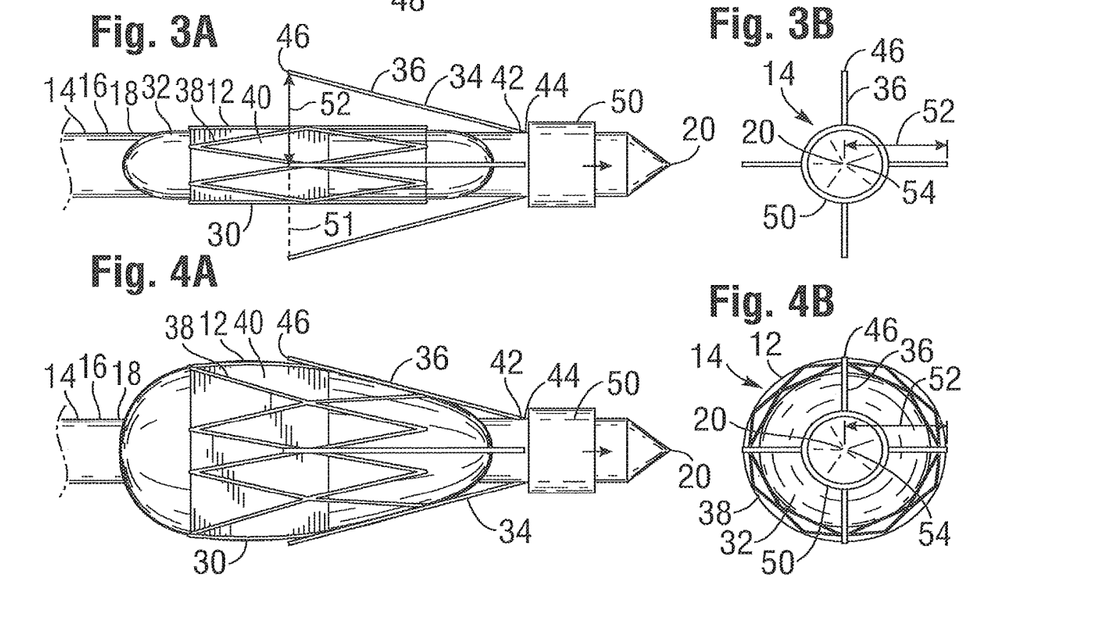
FIGS. 3A-3B depict side and distal end views, respectively, of the system of FIGS. 2A-2B, with the positioning members extended.
FIGS. 4A-4B depict side and distal end views, respectively, of the system of FIGS. 2A-2B, with the balloon expanded to deploy the prosthetic valve.

As depicted in FIGS. 3A-3B, the cuff 50 can be slid distally, thus extending the retractable members 36 away from the catheter 14. The retractable members 36 may be spring-loaded or otherwise biased (e.g., via memory materials, etc.) toward their extended configuration, and/or may be configured to be mechanically extended to the extended configuration via other means known in the art. The free ends 46 of the retractable members 36 are positioned a radial distance 52 away from the radial center 54 of the catheter proximal portion, and are also aligned lengthwise with the alignment position 51 of the prosthetic valve 12.

In one exemplary embodiment of the invention for use with implanting a prosthetic heart valve, the radial distance 52 when the members 36 are retracted (as depicted in FIG. 2A) is about the same as, or just slightly larger than (in order to lie flat on the surface of the valve), the radius of the prosthetic valve when the valve is mounted on the catheter in its crimped/unexpanded/predeployment configuration. For example, for a prosthetic valve which in its unexpanded state has a diameter of 8 mm (i.e., a radius of 4 mm), the radial distance 52 would be about 4 mm or slightly more (e.g., 5 mm). When the members 36 are extended, such as depicted in FIGS. 3A-3B, the radial distance 52 would be about the same as the radius (i.e., one-half of the diameter) of the native heart valve annulus, or slightly larger so that the free ends 46 of the retractable members 36 engage against tissue adjacent the annulus. In an exemplary embodiment, the retractable members when fully extended define a diameter of about 15 mm to 35 mm, so that the radial distance 52 is about 7 mm to 18 mm. Note that other sizes are also within the scope of the invention.

The retractable members 36 serve as guides for the user to determine if the catheter 14 is properly positioned such that the prosthetic valve 12 is properly aligned with the native valve annulus. Once the user determines that the prosthetic valve 12 is in proper position for deployment, he/she can expand the balloon 32 to expand the support stent 38 to its expanded/deployed diameter and thereby deploy the prosthetic heart valve 12, as depicted in FIGS. 4A-4B.

Figure 5:
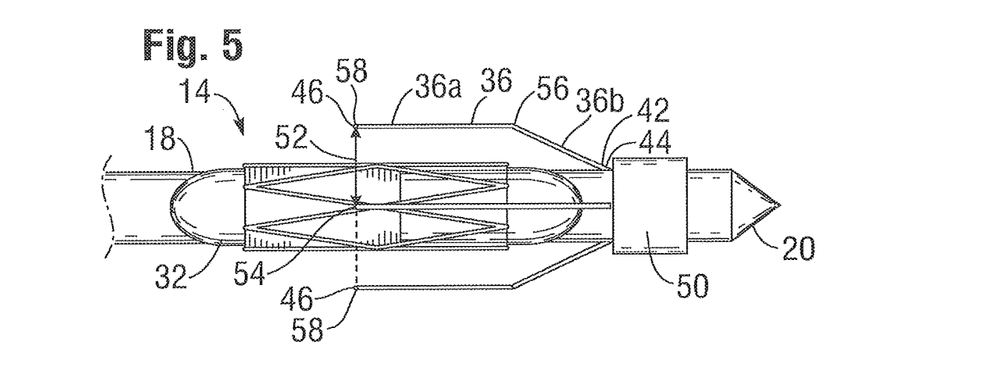
FIG. 5 depicts a side view of a distal portion of a system for replacing a deficient valve, with the positioning members fully extended, according to an embodiment of the invention.

The retractable members may be configured (via spring-loading, hinge connection, and/or memory materials) to assume a somewhat L-shaped and/or curved configuration when extended to their deployed configuration. For example, as depicted in FIG. 5, a catheter 14 has a retractable member 36 (which may have been generally straight from free end to fixed end when in the restrained/unexpanded condition such as in the embodiment depicted in FIGS. 2A-2B) which may include one or more bend/hinge points 56 along its length between generally straight segments 36 *a*, 36 *b* when in an expanded configuration. With the retractable members 36 fully extended and the balloon 32 expanded, the free-end adjacent segment 36 *a* is generally parallel to and adjacent the expanded balloon 32 (and also generally parallel to the catheter distal portion 18), while the fixed-end adjacent segment 36 *b* is angled sharply away from the catheter distal portion 18 to position the free-end adjacent segment 36 *a* at the desired radial distance 52 from the radial center 54. With such a configuration, the free-end adjacent segment 36 *a* can be pressed between the native valve annulus and prosthetic valve 12 when the balloon 32 is expanded, but without substantially interfering with the radial expansion of the prosthetic valve 12 and its support stent 38. Moreover, the free-end adjacent segment 36 *a*, due to its generally parallel orientation, can also be somewhat easily slid out from between the native valve annulus and deployed prosthetic valve 12.

A catheter according to the invention may comprise materials to enhance visibility with various medical imaging techniques, such as fluoroscopy, ultrasound, magnetic resonance, etc. For example, the catheter 14 may include one or more markers for enhanced visibility, such as radiopaque markers, at various positions. In a preferred embodiment, radiopaque markers 58 are included at the free ends 46 of the retractable members 36, as depicted in FIG. 5. The radiopaque markers 58, which are more radiopaque than other portions of the catheter assembly, may assist the user to more clearly see exactly where the retractable members 36 and their associated free ends 46 are positioned. The user can also use the radiopaque marker 58 to visually confirm that the retractable members 36 are radially expanded.

Figure 6A:
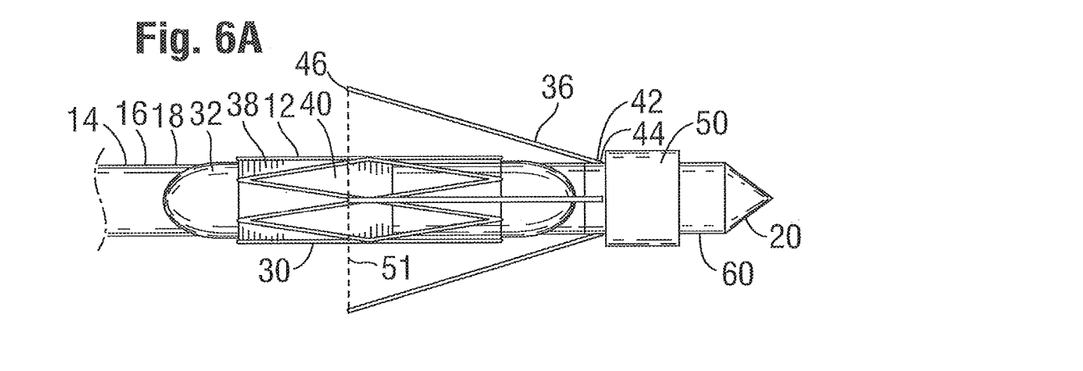
FIG. 6A depicts a side view of a distal portion of a system for replacing a deficient valve according to an embodiment of the invention.
Figure 6B:
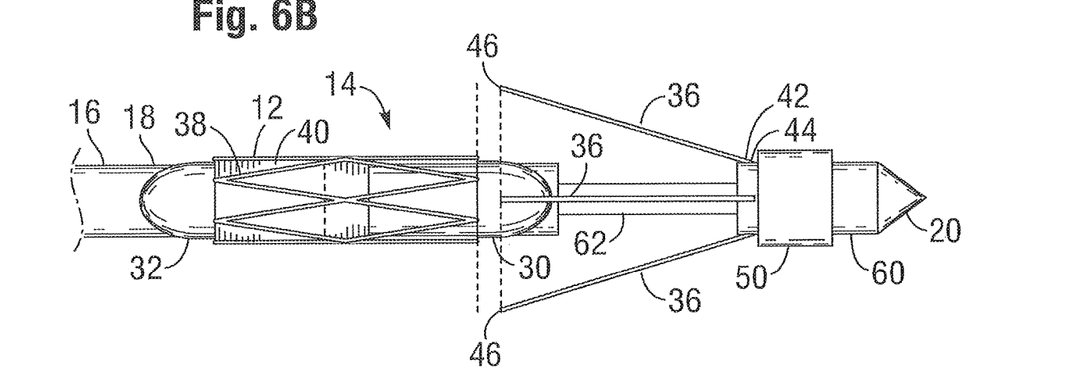
FIG. 6B depicts a side view of the system of FIG. 6A, with a distal end portion of the device extended telescopically from rest of the distal portion.

In another embodiment of the invention, depicted in FIGS. 6A-6B, the catheter 14 includes a slidingly-movable portion 60 which includes the fixed end attachment point 44 to which the fixed end 42 of the retractable member 36 is secured. The slidingly-movable portion 60 can be advanced distally away from (for an embodiment such as depicted in FIGS. 2A-4B) or proximally away from (for an embodiment such as depicted in FIGS. 7A-8B) the implant holding section 30 and/or balloon 32 without requiring movement of the rest of the catheter 32. In a method of using such an embodiment, the user can extend the retractable member(s) 36 to an expanded/deployed position, depicted in FIG. 6A, and use the deployed member(s) 36 to properly position the implant holding section 30 and/or balloon 32 (with prosthetic valve 12 thereon) at the desired deployment location. Once the desired deployment location is achieved, the catheter 12 can be held stationary to keep the (still undeployed) prosthetic valve 12 at the desired deployment location, while the slidingly-movable portion 60 is slid away, via a longitudinally extendable support rod 62, from implant holding section 30 and/or balloon 32 (with prosthetic valve 12 thereon) until the retractable members 36 are largely or entirely clear, with respect to the length of the catheter 12, of the implant holding section 30 and/or balloon 32 (with prosthetic valve 12 thereon), as depicted in FIG. 6B. The prosthetic valve 12 is deployed to its expanded configuration, e.g., by expanding the balloon 32. Note that the expanded balloon 32 and prosthetic valve 12 are clear of the retractable members 36 and the free ends 46 thereof. Before, during, or after deployment of the prosthetic valve 12 and/or expansion of the balloon 32, the retractable members 36 can be retracted to their unexpanded/delivery figuration. With the prosthetic valve 12 deployed, the balloon 32 can be deflated, and the catheter 12 (with deflated balloon and retracted retractable members) can be withdrawn from the patient through the now-deployed prosthetic valve 12.

Figure 7A:
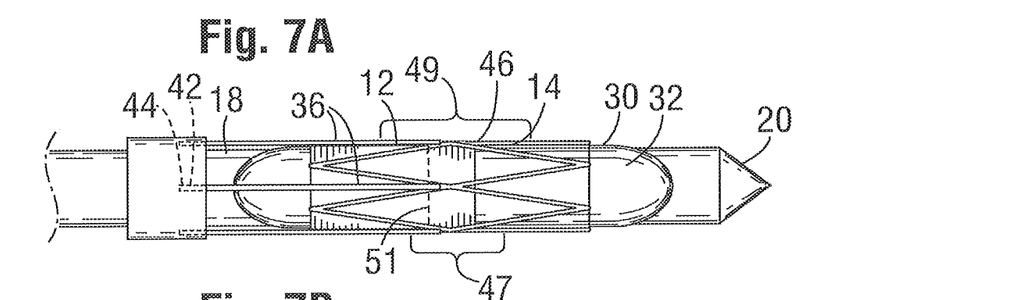
FIGS. 7A-7B depict side views of a distal portion of a system for replacing a deficient valve according to an embodiment of the invention.
Figure 7B:
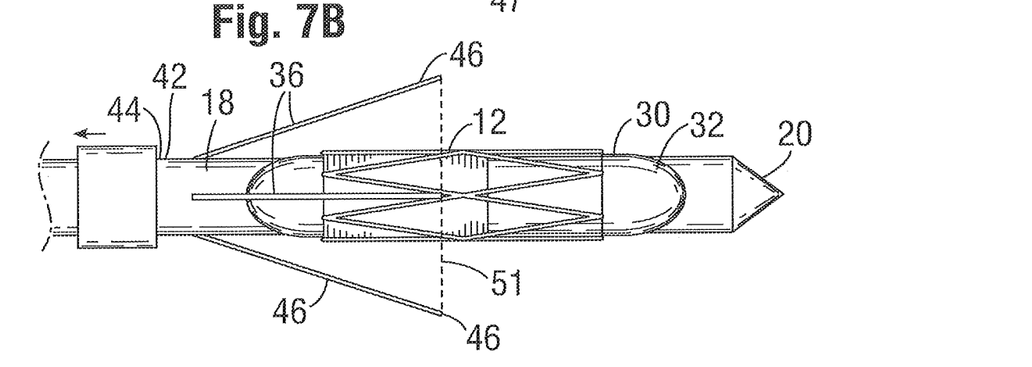

In the embodiments depicted above, the retractable members were secured with their fixed ends distal of the implant holding section. In other embodiments, however, such as those depicted in FIGS. 7A-7B, the retractable members 36 are secured with their fixed ends 42 secured to the catheter distal portion 18 at fixed end attachments points 44 which are proximal of the implant holding section 30, balloon 32, and prosthetic valve 12. When in a retracted configuration (i.e., delivery and/or removal configuration) such as that depicted in FIG. 7A, the free end 46 is positioned radially adjacent the catheter distal portion 18 at a position overlying the prosthetic valve 12 and implant holding section 30/expandable balloon 32. In the particular embodiment depicted, the free end 46 is also positioned longitudinally adjacent the middle third portion 47 of the prosthetic valve 12 and also of the middle third portion 49 of the expandable balloon 32 (which in the particular embodiment depict coincides with a middle third portion of the implant holding section 30). When the retractable members 36 are deployed to the larger deployed configuration, the free ends 46 are in longitudinal alignment with the tissue alignment position 51 of the prosthetic valve.

Figure 8A:
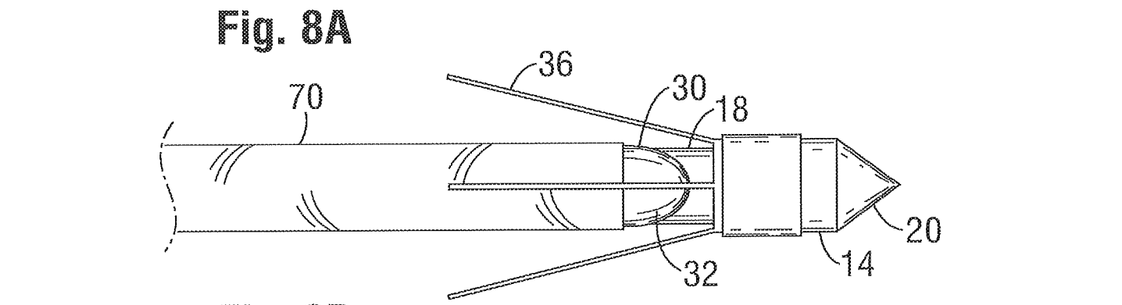
FIGS. 8A-8B depict side views, respectively, of a distal portion of a system for replacing a deficient valve according to an embodiment of the invention.
Figure 8B:
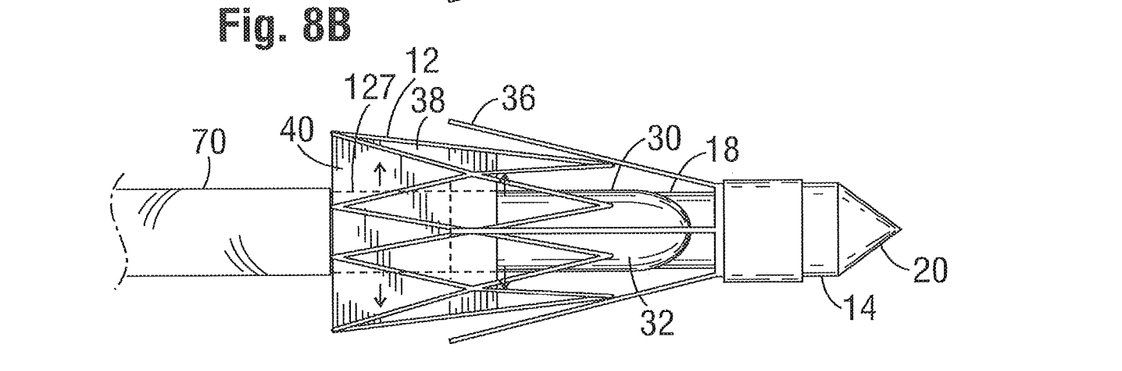

While the above embodiments have depicted an implant such as a prosthetic valve being deployed using a balloon catheter, other deployment methods and devices are also within the scope of the invention. For example, a prosthetic valve 12 or other implant may be a self-expanding device restrained by a sheath 70 configured to be slid over all or a portion of the implant holding section 30 to restrain the prosthetic valve 12 therein, as depicted in FIG. 8A, for delivery of the prosthetic valve 12 to the treatment site. The retractable members 36 can be extended to assist in accurately positioning the prosthetic valve 12, and the sheath 70 can then be slidingly retracted from the implant holding section to release the prosthetic valve 12, which then self-expands, as depicted in FIG. 8B. The self-expanding support structure 38 of the prosthetic valve 12 thus expands into contact with the native valve annulus.

Figure 9A:
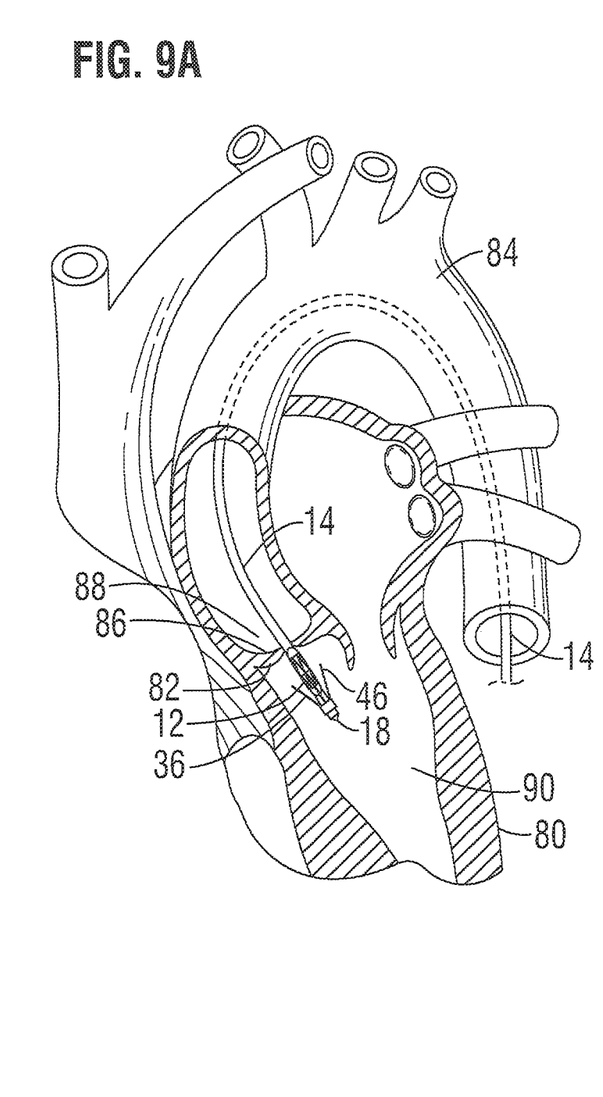
FIGS. 9A-9B depict cross-sectional views through the left side of a patient's heart showing a prosthetic valve being delivered and deployed to a native valve annulus via a retrograde approach according to an embodiment of the invention.
Figure 9B:
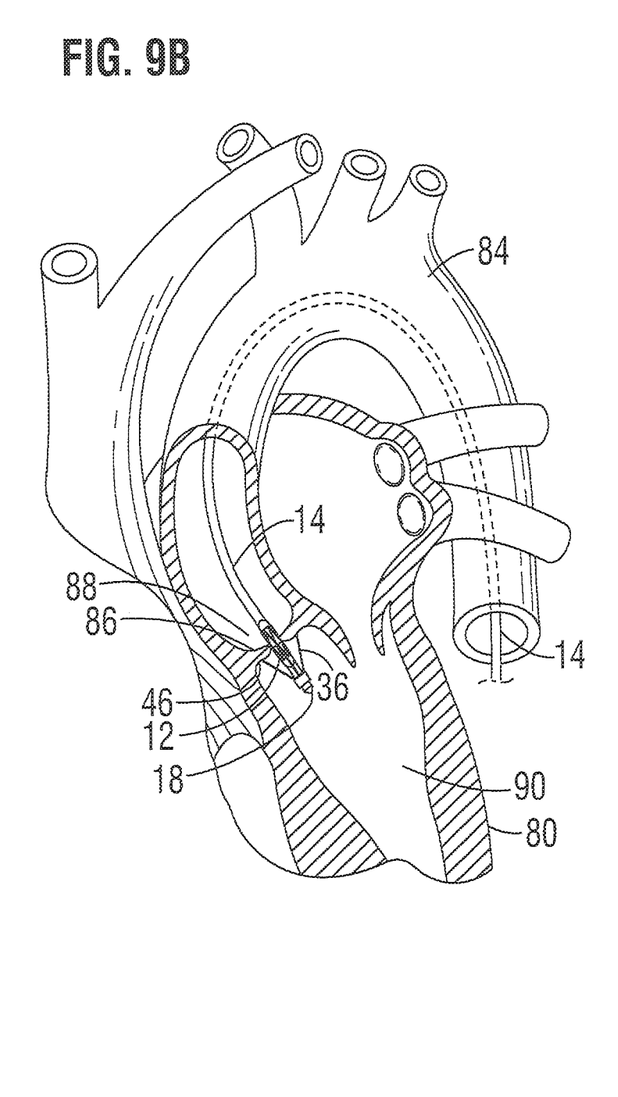

FIGS. 9A-9B depict a catheter 14 (similar to that depicted in FIGS. 2A-2B) delivering a prosthetic valve 12 into a heart 80 for deployment within the native valve annulus 82 via a retrograde approach according to an embodiment of the invention. The catheter 14 is advanced into the patient via the femoral artery (not shown) and then through the aorta 84 and aortic sinus 88, through the native valve annulus 82 and native valve leaflets 86, and into the left ventricle 90. Once the free ends 46 of the retractable members 36 have cleared the valve annulus 82, as depicted in FIG. 9A, the retractable members 36 can be deployed/radially extended. The user can then slowly retract the catheter 14 until the free ends 46 contact the native valve annulus 82, native valve leaflets 86, and/or other valve or valve-adjacent tissue, as depicted in FIG. 9B. Using tactile feedback from the catheter 14 created by the contact of the free ends 36 with the valve tissue and/or valve-adjacent tissue, the user can confirm the proper positioning of the prosthetic valve 12. With the proper positioning confirmed, the user can expand the balloon 32 or otherwise (e.g., via removal of a restraining sheath, etc.) effectuate expansion/deployment of the prosthetic valve 12 into the desired position within the native valve annulus 82. The retractable members 36 are retracted back to their restrained/unexpanded configuration, the balloon 32 is deflated to a reduced diameter, and the catheter 14 is then withdrawn from the heart, leaving the prosthetic valve deployed within the heart.

Note that the user may rely on additional positioning techniques, such as fluoroscopy, echocardiography, etc. For example, during initial advancement of the catheter into the heart, the user may use fluoroscopic, echocardiagraphic, and/or other imaging methods to provide visual confirmation of the orientation and position of the catheter, prosthetic valve, and/or positioning elements relative to the native valve annulus or other deployment site. The user may also use the fluoroscopic, echocardiagraphic, and/or other imaging methods to provide visual confirmation of the orientation and position of various elements of the delivery system in addition to the tactile feedback provided by the positioning elements, e.g., during the positioning of the device described herein using the positioning elements. The tactile feedback thus provides the operator with another important sensory cue to the relative position of the positioning elements/prosthetic valve with respect to the native valve annulus.

While the specific methods discussed above address replacement of an aortic valve, the invention can be used to aid in the accurate positioning and deployment of implants relative to all cardiac valves, as well as relative to other orifices and body lumens, such as the orifices of all the major arteries and veins related to the heart (including but not limited to the superior and inferior vena cavae, pulmonary arteries and veins, coronary sinus, inominate artery, common carotid arteries, and subclavian arteries.

Figure 10A:
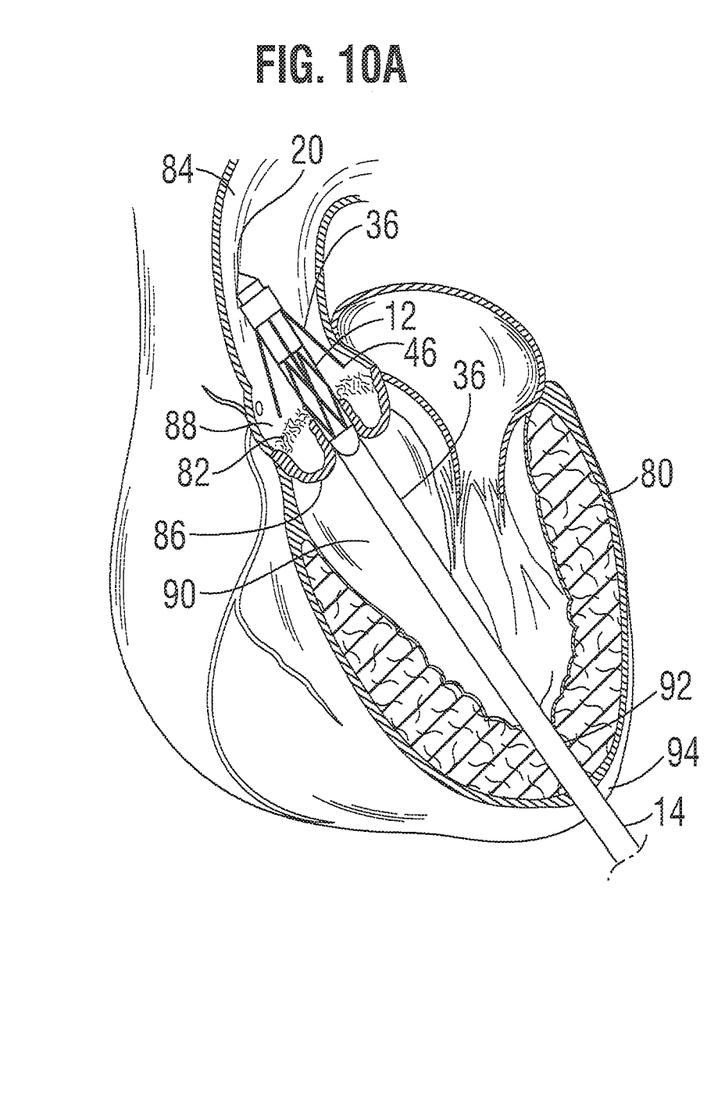
FIGS. 10A-10B depict cross-sectional views through the left side of a patient's heart showing a prosthetic valve being delivered and deployed to a native valve annulus via an antegrade transapical approach according to an embodiment of the invention.
Figure 10B:
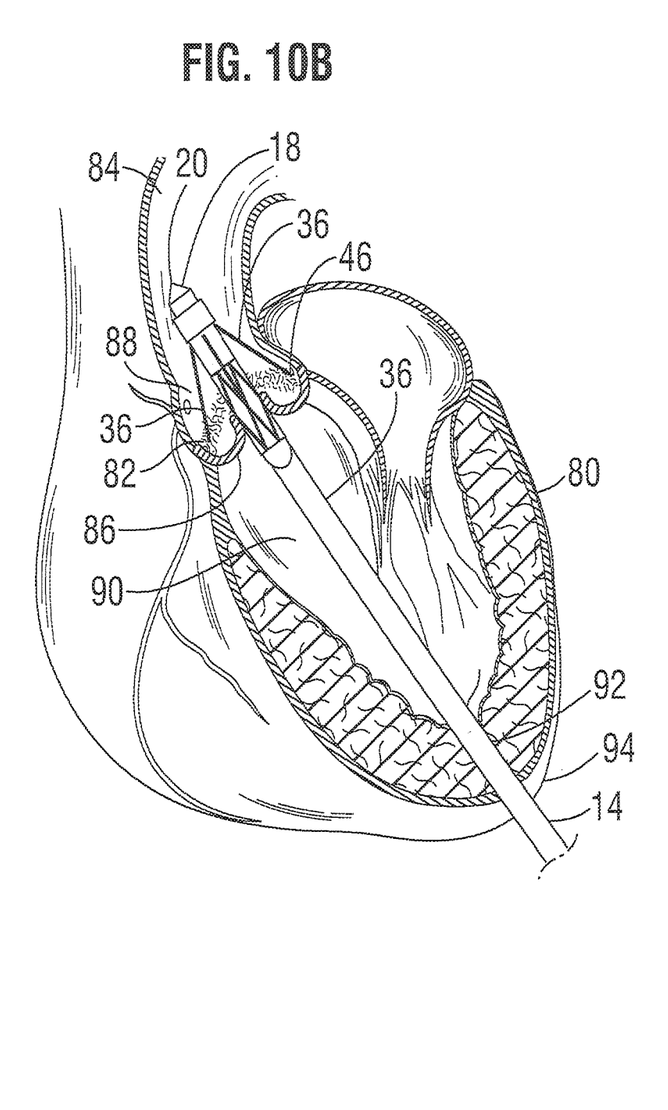

FIGS. 10A-10B depict a catheter 14 (similar to that depicted in FIGS. 2A-2B) delivering a prosthetic valve 12 into a heart 80 for deployment within the native valve annulus 82 via an antegrade approach according to an embodiment of the invention. The catheter 14 is advanced into the patient via an intercostal incision (not shown) and then through a puncture 92 in the apex 94 of the heart 80 and into the left ventricle 90. The catheter 14 is then advanced through the native valve annulus 82 and native valve leaflets 86, and into the aortic sinus 88 and aorta 84. Once the free ends 46 of the retractable members 36 have cleared the valve annulus 82, as depicted in FIG. 10A, the retractable members 36 can be deployed/radially extended. The user can then slowly retract the catheter 14 until the free ends 46 contact the native valve annulus 82, native valve leaflets 86, and/or other valve or valve-adjacent tissue, as depicted in FIG. 10B. Using tactile feedback from the catheter 14 created by the contact of the free ends 36 with the valve tissue and/or valve-adjacent tissue, the user can confirm the proper positioning of the prosthetic valve 12. With the proper positioning confirmed, the user can expand the balloon 32 or otherwise (e.g., via removal of a restraining sheath, etc.) effectuate expansion/deployment of the prosthetic valve 12 into the desired position within the native valve annulus 82. The retractable members 36 are retracted back to their restrained/unexpanded configuration, the balloon 32 is deflated to a reduced diameter, and the catheter 14 is then withdrawn from the heart, leaving the prosthetic valve deployed within the heart. The apical puncture 92, intercostal incision, and other incisions are closed (e.g., via suturing) to complete the procedure.

Figure 11A:
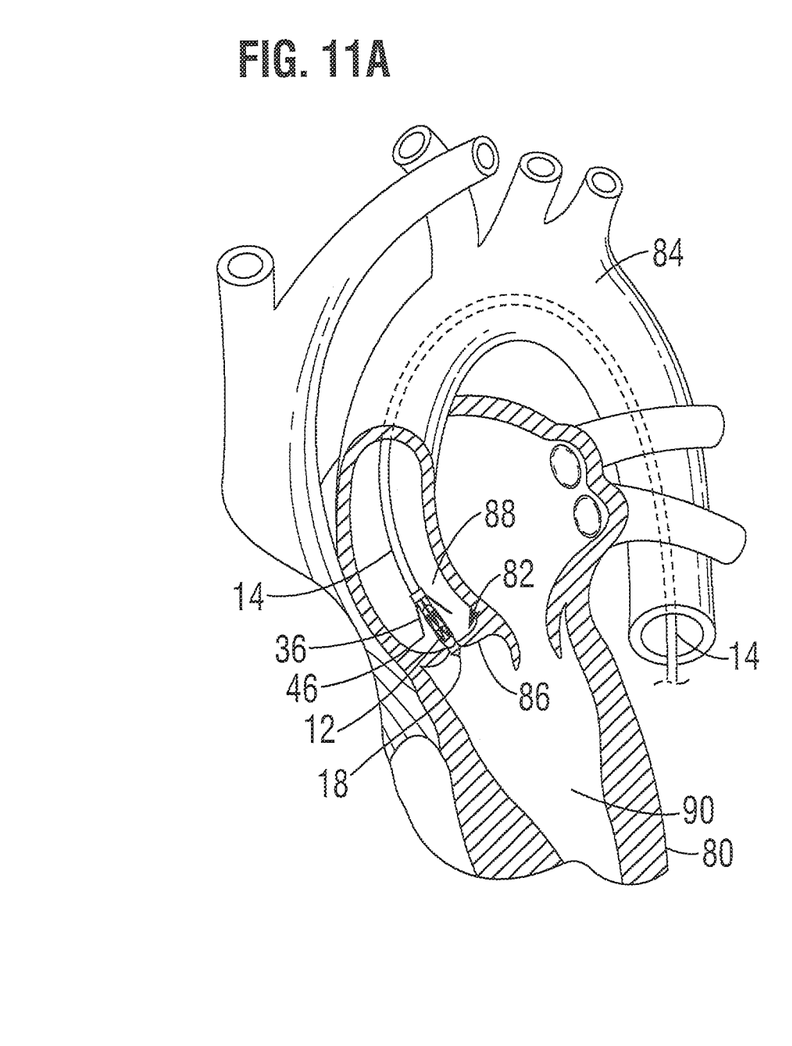
FIGS. 11A-11B depict cross-sectional views through the left side of a patient's heart showing a prosthetic valve being delivered and deployed to a native valve annulus via a retrograde approach according to an embodiment of the invention.
Figure 11B:
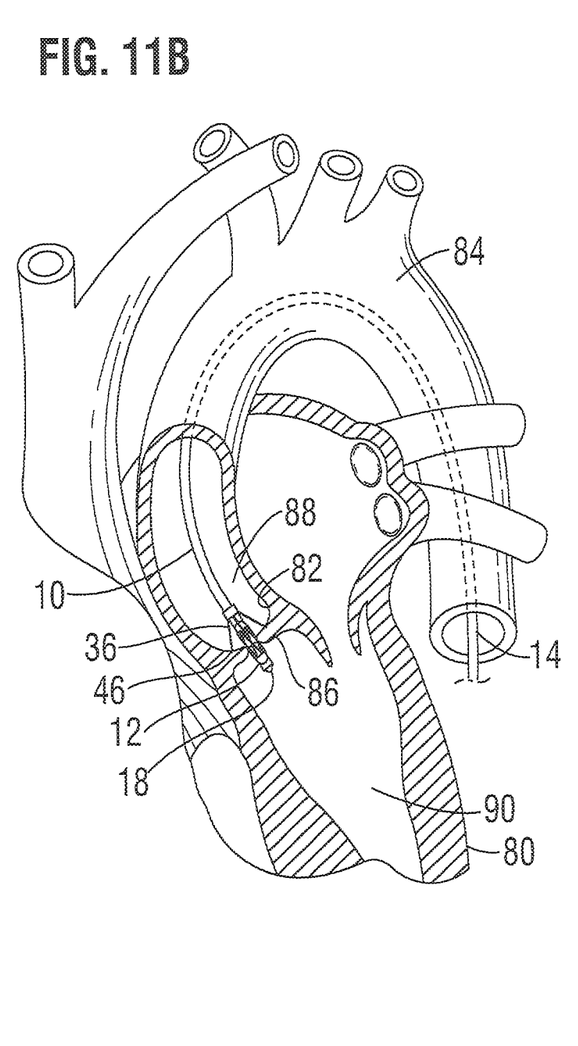

FIGS. 11A-11B depict a catheter 14 (similar to that depicted in FIGS. 7A-8B) delivering a prosthetic valve 12 into a heart 80 for deployment within the native valve annulus 82 via a retrograde approach according to an embodiment of the invention. The catheter 14 is advanced into the patient via the femoral artery (not shown) and then through the aorta 84 to a position where the retractable members 36 are in the coronary sinus 88 and just short of the native valve annulus 82 and native valve leaflets 86. The distal end 18 of the catheter 14 may be positioned just short of, within, or through the native valve annulus 82. The retractable members 36 (which extend with the free ends 36 thereof facing distally with respect to the catheter 12) are then deployed/radially extended, as depicted in FIG. 11A. The user can then slowly advance the catheter 14 until the free ends 46 contact the native valve annulus 82, native valve leaflets 86, and/or other valve or valve-adjacent tissue, as depicted in FIG. 11B. Using tactile feedback from the catheter 14 created by the contact of the free ends 36 with the valve tissue and/or valve-adjacent tissue, the user can confirm the proper positioning of the prosthetic valve 12. With the proper positioning confirmed, the user can expand the balloon 32 or otherwise (e.g., via removal of a restraining sheath, etc.) effectuate expansion/deployment of the prosthetic valve 12 into the desired position within the native valve annulus 82. The retractable members 36 are retracted back to their restrained/unexpanded configuration, the balloon 32 is deflated to a reduced diameter, and the catheter 14 is then withdrawn from the heart, leaving the prosthetic valve 12 deployed within the heart.

Figure 12A:
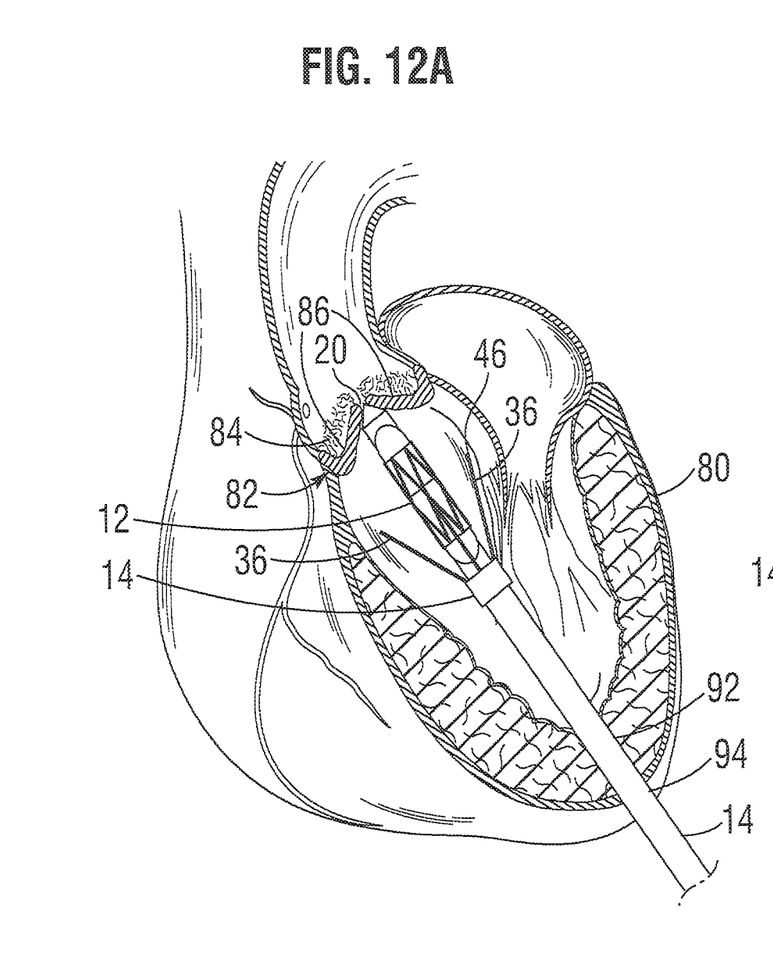
FIGS. 12A-12B depict cross-sectional views through the left side of a patient's heart showing a prosthetic valve being delivered and deployed to a native valve annulus via an antegrade transapical approach according to an embodiment of the invention.
Figure 12B:
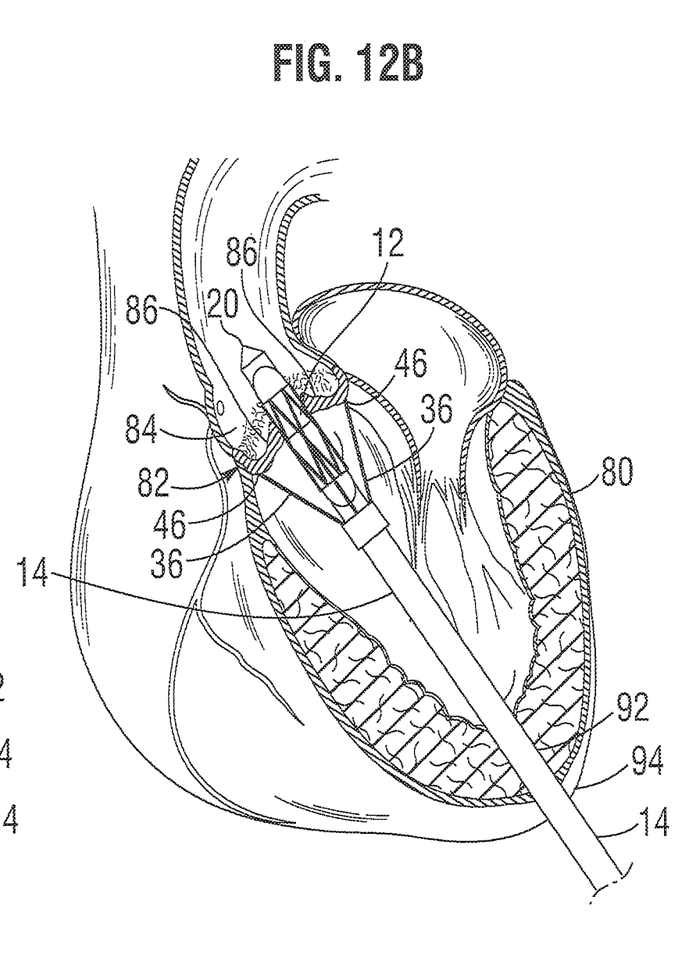

FIGS. 12A-12B depict a catheter 14 (similar to that depicted in FIGS. 7A-7B) delivering a prosthetic valve 12 into a heart 80 for deployment within the native valve annulus 82 via an antegrade approach according to an embodiment of the invention. The catheter 14 is advanced into the patient via an intercostal incision (not shown) and then through a puncture 92 in the apex 94 of the heart 80 and into the left ventricle 90. The catheter 14 is then advanced toward the native valve annulus 82 and native valve leaflets 86, but stopping with the free ends 46 of the retractable members 36 just short thereof. With the free ends 46 just short of the native valve annulus 82, as depicted in FIG. 12A, the retractable members 36 can be deployed/radially extended. The user can then slowly advance the catheter 14 until the free ends 46 contact the native valve annulus 82, native valve leaflets 86, and/or other valve or valve-adjacent tissue, as depicted in FIG. 12B. Using tactile feedback from the catheter 14 created by the contact of the free ends 46 with the valve tissue and/or valve-adjacent tissue, the user can confirm the proper positioning of the prosthetic valve 12. With the proper positioning confirmed, the user can expand the balloon (not shown) or otherwise (e.g., via removal of a restraining sheath, etc.) effectuate expansion/deployment of the prosthetic valve 12 into the desired position within the native valve annulus 82. The retractable members 36 are retracted back to their restrained/unexpanded configuration, the balloon is deflated to a reduced diameter, and the catheter 14 is then withdrawn from the heart 80, leaving the prosthetic valve 12 deployed within the native valve annulus 82. The apical puncture 92, intercostal incision, and other incisions are closed (e.g., via suturing) to complete the procedure.

Other devices and methods are also within the scope of the invention, as well is the use of various materials to form aspects thereof. For example, the retractable members may be formed from materials such as metal and/or plastic. The retractable members may be attached to the delivery catheter through an inner lumen, with a control line passing through the inner lumen back to the handle and to the retractable member controls. The number of retractable members extending from the catheter may range from 1 to 16 or more. The retractable members may be equally spaced about the circumference of the catheter body. The retractable members may be spring-loaded or otherwise biased toward an expanded configuration, such that releasing them from a restrained configuration (such as by withdrawing a restraining sheath, or advancing the members out of a lumen) results in deployment of the retractable members radially outward from the catheter body. The retractable members may be inflatable, wherein when uninflated they lie generally flat against the catheter but when inflated they assume their expanded/deployed configuration with the free ends displaced radially away from the catheter body. The retractable members may be deployed and/or retracted using a combination of the above-discussed methods. For example, member deployment could be achieved via spring-loading and/or memory aspects of the member material, while member retraction could be achieved by retracting the members into a restraining sheath.

The retractable members may have rounded free ends to prevent tissue trauma from contact with the free ends. For example, the retractable members may be looped structures, similar in form to a wire kitchen whisk, forming smooth, rounded contact surfaces on the free ends of each retractable member.

Figure 13A:
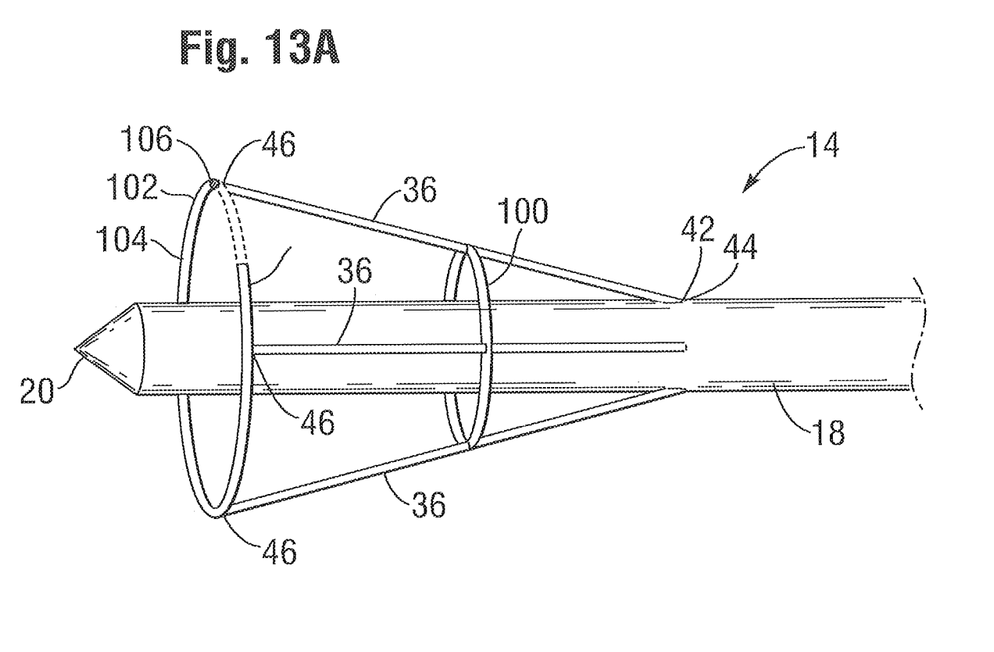
FIGS. 13A-13B depict side (in partial cross-section) and distal end views, respectively, of a distal portion of a device according to an embodiment of the invention.
Figure 13B:
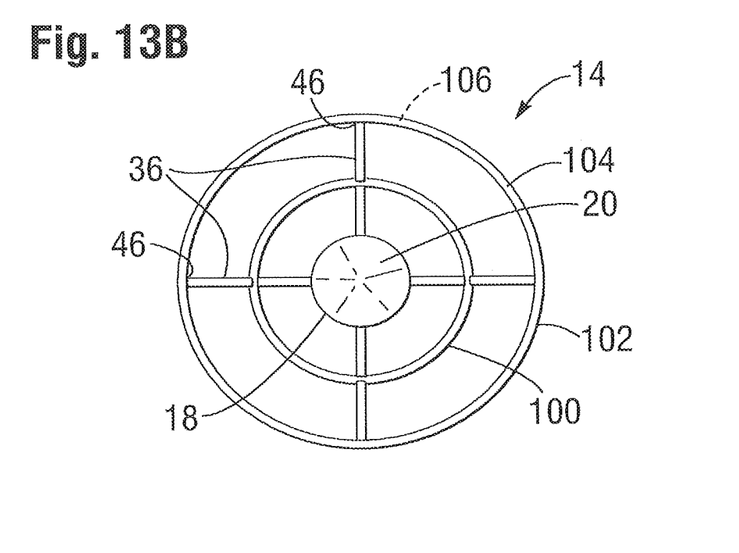

In a further embodiment depicted in FIGS. 13A-13B, the retractable members 36 of a catheter 14 may all be interconnected, or tethered, to each other via one or more tethers 100, 102, so that when the retractable members 36 are expanded the resulting contact surface 104 presented to the native valve annulus (or other tissue) by the tether 102 connecting the free ends 46 is a smooth, circular surface. The overall structure created by the deployed retractable members 36 and tethers 100, 102 would thus resemble a cone, such as a badminton shuttlecock, along a central axis coinciding with a central axis of the catheter. One or more of the tethers, and particularly the tether 102 between the free ends 46, may each form a continuous, hollow, and inflatable space 106 which can hold a fluid. When the inflatable tether ring 102 is inflated with a fluid solution, the free ends 46 are prevented from contacting the tissue of the valve annulus (or other tissue) and instead all tissue contact is with the inflatable ring 102, which presents a smooth, atraumatic contact surface 104 to reduce local trauma. The fluid solution may comprise a radiographic contrast solution to permit enhanced fluoroscopic visualization.

While in the detailed descriptions above the systems and methods is described for replacing a native valve, the systems and methods of the invention could also be used to replace previously-deployed prosthetic devices, such as a previously-deployed prosthetic heart valve which was failing due to structural and/or other failure/damage.

While the invention has been described in various embodiments, it is to be understood that the words which have been used are words of description and not of limitation. Therefore, changes may be made within the appended claims without departing from the true scope of the invention.

The invention claimed is:

1. A method of delivering a prosthetic valve to a position within a heart of a patient, comprising:
    advancing a catheter to a native valve annulus position within the heart of the patient;
    deploying at least one extendable positioner positioned at a distal end of the catheter from a first position to a second position, wherein the at least one extendable positioner extends radially away from the catheter to the second position;
    confirming that the prosthetic valve is in proper position in alignment with or adjacent to the native valve annulus by using tactile feedback from the catheter created by contact of a free end of the at least one extendable positioner with native valve tissue;

wherein the catheter includes a slidingly-movable portion which includes a fixed end attachment point to which a fixed end of the at least one extendable positioner is secured, the slidingly-moveable portion being moveable without requiring movement of the rest of the catheter;

after confirming that the prosthetic valve is in proper position and while holding the prosthetic valve stationary in position, sliding the slidingly-movable portion via an extendable support rod away from an implant holding section and/or balloon until the at least one extendable positioner is clear of the implant holding section and/or balloon; and deploying the prosthetic valve into a desired position within the native valve annulus.

2. The method of claim 1, further comprising:

retracting the at least one extendable positioner back to the first position; and withdrawing the catheter from the heart.

3. The method of claim 1, further comprising:

directing the catheter percutaneously through an intercostal opening in a body of the patient; and puncturing an opening into a left ventricular apex of the heart of the patient.

4. The method of claim 1, wherein the at least one extendable positioner is spring loaded or biased toward the second position.

5. The method of claim 1, further comprising directing the catheter into the heart of the patient via a femoral artery.

6. The method of claim 1, wherein the prosthetic valve is self-expanding and restrained by a retractable sheath, and the method further comprises:

sliding the retractable sheath to deploy the prosthetic valve.

7. The method of claim 1, further comprising:

expanding a balloon to deploy the prosthetic valve into the desired position.

8. The method of claim 7, further comprising:

controlling the catheter and balloon using one or more controls on a catheter handle located on a proximal portion of the catheter.

9. A method of delivering a prosthetic valve to a desired position within a patient, comprising:

advancing a catheter to a native valve annulus position within a heart of the patient;

deploying a plurality of extendable positioners positioned at a distal end of the catheter from a first position to a second position, wherein the extendable positioners extend radially away from the catheter to the second position;

confirming that the prosthetic valve is properly positioned in alignment with or adjacent to the native valve annulus using tactile feedback from the extendable positioners, caused by contact of a free end of at least one extendable positioner with native valve tissue;

wherein the catheter includes a slidingly-movable portion which includes a fixed end attachment point to which fixed ends of the extendable positioners are secured, and the slidingly-movable portion can be advanced away from an implant holding section and/or a balloon without substantially moving the rest of the catheter, the method further comprising holding the catheter stationary to keep the undeployed prosthetic valve at a desired deployment location;

after confirming that the prosthetic valve is properly positioned in alignment with or adjacent to the native valve annulus using the extendable positioners, sliding the slidingly-movable portion away from valve implant holding section and/or balloon until the extendable positioners are clear, with respect to a length of the catheter, of the implant holding section and/or balloon; and deploying the prosthetic valve into a desired position within the native valve annulus.

10. The method of claim 9, further comprising retracting the extendable positioners back to the first position; and removing the catheter from a body of the patient.

11. The method of claim 9, wherein the prosthetic valve is a transcatheter heart valve.

12. The method of claim 11, wherein the advancing further comprises:

creating an intercostal incision in the patient;

puncturing an apex of the heart; and advancing the catheter through a native valve annulus and into an aorta.

13. The method of claim 11, wherein the advancing comprises:

advancing the catheter into the patient through a femoral artery, an aorta and through a native valve annulus, and into a left ventricle, respectively.

14. The method of claim 9, wherein the extendable positioners are spring-loaded or biased toward the second position.

15. The method of claim 9, wherein the fixed ends of the plurality of extendable positioners are attached to a telescopically slidingly-movable portion of the catheter, the method further comprising:

holding the device stationary at the desired location;

extending the telescopically slidingly-movable portion of the catheter via an extendable support rod in a direction away from an implant-holding section of the catheter until a majority of the plurality of extendable positioners are clear of the implant-holding section of the catheter.

16. The method of claim 9, wherein at least some of the extendable positioners comprise a shape-memory material and are self-expanding.

17. A method of delivering an implant to a position within the heart of a patient, comprising:

advancing a catheter to a position within a heart of the patient;

deploying at least one extendable positioner positioned at a distal end of the catheter from a first position to a second position, wherein the at least one extendable positioner extends radially away from the catheter to the second position;

confirming that the implant is in proper position in the heart by using feedback from the catheter created by contact of a free end of the at least one extendable positioner with native tissue;

wherein the catheter includes a slidingly-movable portion which includes a fixed end attachment point to which a fixed end of the at least one extendable positioner is secured, the slidingly-moveable portion being moveable without moving an implant-holding section and/or balloon of the catheter;

while holding the implant in position, sliding the slidingly-movable portion away from the implant holding section and/or balloon until the at least one extendable positioner is clear of the implant holding section and/or balloon; and deploying the implant into a desired position within the heart.

18. The method of claim 17, further comprising:
retracting the at least one extendable positioner back to the first position; and
withdrawing the catheter from the heart.

19. The method of claim 17, further comprising:
directing the catheter percutaneously through an intercostal opening in a body of the patient; and
puncturing an opening into a left ventricular apex of the heart of the patient.

20. The method of claim 17, wherein the at least one extendable positioner is spring loaded or biased toward the second position.

21. The method of claim 17, further comprising directing the catheter into the heart of the patient via a femoral artery.

22. The method of claim 17, wherein the at least one extendable positioner comprises a shape-memory material and is self-expanding.

\* \* \* \* \*